(12) United States Patent
Wu et al.

(10) Patent No.: US 10,228,891 B2
(45) Date of Patent: Mar. 12, 2019

(54) METHOD AND APPARATUS FOR CONTROLLING DISPLAY DEVICE, AND INTELLIGENT PAD

(71) Applicant: Xiaomi Inc., Beijing (CN)

(72) Inventors: Ke Wu, Beijing (CN); Xinyu Liu, Beijing (CN)

(73) Assignee: Xiaomi Inc., Beijing (CN)

( * ) Notice: Subject to any disclaimer, the term of this patent is extended or adjusted under 35 U.S.C. 154(b) by 129 days.

(21) Appl. No.: 15/135,260

(22) Filed: Apr. 21, 2016

(65) Prior Publication Data

US 2017/0049360 A1    Feb. 23, 2017

(30) Foreign Application Priority Data

Aug. 20, 2015   (CN) .......................... 2015 1 0515888

(51) Int. Cl.
*G06F 3/14* (2006.01)
*G06F 3/041* (2006.01)
(Continued)

(52) U.S. Cl.
CPC ................ *G06F 3/14* (2013.01); *A47C 31/00* (2013.01); *A61B 5/01* (2013.01); *A61B 5/103* (2013.01);
(Continued)

(58) Field of Classification Search
CPC ......... A61B 5/103; A61B 5/01; A61B 5/6892; A61B 5/1172; A61B 5/1118;
(Continued)

(56) References Cited

U.S. PATENT DOCUMENTS 8,640,021 B2    1/2014 Perez et al.
2002/0184500 A1  12/2002 Maritzen et al.
(Continued)

FOREIGN PATENT DOCUMENTS

CN        1554165 A     12/2004
CN      101499106 A      8/2009
(Continued)

OTHER PUBLICATIONS

Wilson, J. D., Buffa, A. J. (2003). College Physics (5th), Saddlebrook, NJ: Pearson Education. ISBN 0-13-067644-6. Chapter 9 pp. 312-313 (hereinafter "Wilson").*
(Continued)

*Primary Examiner* — Darlene M Ritchie
(74) *Attorney, Agent, or Firm* — Oblon, McClelland, Maier & Neustadt, L.L.P.

(57) ABSTRACT

The disclosure relates to a method and apparatus for controlling a display device. Aspects of the disclosure provide a method controlling a display device. The method includes detecting an object on a pad; determining whether the object is a user; determining an identity of the user when it is determined that the object is the user; determining at least one user preference associated with the user based on the identity of the user; and transmitting, to the display device, at least one instruction to display information associated with the at least one user preference. When determining the identity of the user, the method includes determining that the user is a person.

11 Claims, 17 Drawing Sheets

(51) Int. Cl.
*A61B 5/103* (2006.01)
*A47C 31/00* (2006.01)
*A61B 5/01* (2006.01)
*A61B 5/1172* (2016.01)
*A61B 5/00* (2006.01)
*H04N 21/258* (2011.01)
*H04N 21/422* (2011.01)
*H04N 21/466* (2011.01)
*A61B 5/11* (2006.01)
*A63F 13/214* (2014.01)
*H04N 21/442* (2011.01)

(52) U.S. Cl.
CPC .......... *A61B 5/1172* (2013.01); *A61B 5/6892* (2013.01); *A63F 13/214* (2014.09); *G06F 3/0414* (2013.01); *H04N 21/25866* (2013.01); *H04N 21/42201* (2013.01); *H04N 21/44218* (2013.01); *H04N 21/4668* (2013.01); *A61B 5/1118* (2013.01)

(58) Field of Classification Search
CPC ...... G06F 3/0414; G06F 3/14; G06F 19/3475; A47C 31/00; H04N 21/42201; H04N 21/25866; H04N 21/4668; H04N 21/44218; A63F 13/214
See application file for complete search history.

(56) References Cited

U.S. PATENT DOCUMENTS

| | | | |
|---|---|---|---|
| 2004/0172290 A1* | 9/2004 | Leven | A61B 5/0006 705/2 |
| 2008/0230497 A1 | 9/2008 | Strickland et al. | |
| 2008/0278408 A1 | 11/2008 | Strickland et al. | |
| 2009/0091529 A1 | 4/2009 | Do et al. | |
| 2010/0045609 A1 | 2/2010 | Do | |
| 2010/0216601 A1* | 8/2010 | Saalasti | A61B 5/024 482/8 |
| 2012/0124456 A1 | 5/2012 | Perez et al. | |
| 2013/0171601 A1* | 7/2013 | Yuasa | A61B 5/1114 434/258 |
| 2014/0088995 A1* | 3/2014 | Damani | G06F 19/3418 705/2 |
| 2014/0148709 A1* | 5/2014 | Gu | A61B 5/1171 600/479 |
| 2014/0359647 A1* | 12/2014 | Shoemake | H04N 5/23206 725/10 |
| 2015/0039259 A1 | 2/2015 | Park et al. | |
| 2015/0143435 A1* | 5/2015 | Kim | H04N 21/25891 725/86 |
| 2015/0161911 A1* | 6/2015 | Muto | G06F 17/30554 434/127 |
| 2015/0242008 A1* | 8/2015 | Beckman | G06F 3/043 345/177 |
| 2015/0256877 A1* | 9/2015 | Yoneda | G06Q 30/02 725/34 |
| 2015/0282766 A1* | 10/2015 | Cole | A61B 5/7267 702/139 |
| 2015/0320362 A1* | 11/2015 | Hasegawa | A61B 5/0205 600/529 |
| 2016/0022218 A1 | 1/2016 | Hayes et al. | |
| 2016/0070392 A1* | 3/2016 | Wang | H03K 17/9643 345/173 |
| 2016/0106351 A1* | 4/2016 | Liao | A61B 5/14552 600/301 |
| 2016/0120461 A1* | 5/2016 | Kato | G06Q 10/10 600/301 |
| 2017/0134778 A1* | 5/2017 | Christie | H04N 21/2541 |
| 2017/0212552 A1* | 7/2017 | Stotler | G06F 1/163 |
| 2018/0202873 A1* | 7/2018 | Bonifas | G01L 1/14 |

FOREIGN PATENT DOCUMENTS

| | | |
|---|---|---|
| CN | 101681494 A | 3/2010 |
| CN | 101744693 A | 6/2010 |
| CN | 102523401 A | 6/2012 |
| CN | 102541257 A | 7/2012 |
| CN | 102591303 A | 7/2012 |
| CN | 102824052 A | 12/2012 |
| CN | 103142219 A | 6/2013 |
| CN | 103932798 A | 7/2014 |
| CN | 104108393 A | 10/2014 |
| CN | 104622476 A | 5/2015 |
| CN | 105117007 A | 12/2015 |
| JP | 2014-502454 A | 1/2014 |
| KR | 10-2013-0125367 A | 11/2013 |
| RU | 2463936 C2 | 10/2012 |
| WO | 2014151577 A1 | 9/2014 |
| WO | 2015037186 A1 | 3/2015 |

OTHER PUBLICATIONS

International Search Report dated May 24, 2016 in PCT/CN2015/098920 (submitting English translation only).
Written Opinion dated May 24, 2016 in PCT/CN2015/098920.
Partial European Search Report dated Jan. 11, 2017 in Patent Application No. 16184958.3.
Thiago Teixeira, et al., "A Survey of Human-Sensing: Methods for Detecting Presence, Count, Location, Track, and Identity" ACM Computing Surveys, XP055101195, Sep. 1, 2010, 35 Pages.
Lee Middleton, et al., "A Floor Sensor System for Gait Recognition" Automatic Identification Advanced Technologies, Fourth IEEE Workshop on Buffalo, Piscataway, NY, XP010856517, Oct. 17, 2005, 6 Pages.
Office Action dated Jul. 10, 2017 in Korean Patent Application No. 10-2016-7022227.
Notification of the First Office Action dated Sep. 12, 2017 in Chinese Patent Application No. 201510515888.7 (with unedited computer generated English translation).
Supplementary European Search Report in European application No. 16184958.3, dated Mar. 16, 2017 .
Andreas Riener et al:"Supporting Implicit Human-to-Vehicle Interaction: Driver Identification from Sitting Postures", Proceedings of the Fiirst Annual International Symposium on Vehicular Computing Systems, Jul. 22, 2008 (Jul. 22, 2008), XP055351946, Gent, Belgium DOI:10.4108/ICST ISVCS2008.3545.
Notification of the First Office Action of Mexican application No. MX/A/2016/006400, dated Mar. 1, 2018.
Notification of the First Office Action of Russian application No. 2016121391 , dated Mar. 26, 2018.
Japanese Office Action dated Nov. 24, 2017 in Japanese Patent Application No. 2016-552904 (with unedited computer generated English translation), 9 pages.

* cited by examiner

METHOD AND APPARATUS FOR CONTROLLING DISPLAY DEVICE, AND INTELLIGENT PAD

CROSS-REFERENCE TO RELATED APPLICATIONS

This application is filed based on and claims priority to Chinese Patent Application 201510515888.7 filed on Aug. 20, 2015, the entire contents of which are incorporated herein by reference in its entirety.

TECHNICAL FIELD

The present disclosure relate to the technical field of intelligent homes, and more particularly to a method and apparatus for controlling a display device, and an intelligent pad.

BACKGROUND

Generally, a user is used to opening a display device to view and select information that the user prefers when lying or sitting on a pad in daily life, wherein the pad may be a mattress, a seat cushion, a sofa cushion and so on. Taking a mattress for example, the user usually gets used to opening a display device to search a television show, a movie, an electronic book and so on that the user prefers when lying on the mattress. However, low searching efficiency and poor user experience are caused by a large amount of information when the user sits or lies on a pad.

SUMMARY

This Summary is provided to introduce a selection of aspects of the present disclosure in a simplified form that are further described below in the Detailed Description. This Summary is not intended to identify key features or essential features of the claimed subject matter, nor is it intended to be used to limit the scope of the claimed subject matter.

Aspects of the disclosure provide a method controlling a display device. The method includes detecting an object on a pad; determining whether the object is a user; determining an identity of the user when it is determined that the object is the user; determining at least one user preference associated with the user based on the identity of the user; and transmitting, to the display device, at least one instruction to display information associated with the at least one user preference. When determining the identity of the user, the method includes determining that the user is a person.

When determining whether the object is the user, the method includes acquiring temperature data of the object; determining whether the temperature data is within a pre-stored temperature range of a human body; and determining that the object is the person when the temperature data is determined to be within the pre-stored temperature range of the human body.

When determining whether the object is the user, the method also includes acquiring pressure data from a plurality of locations on the pad; determining a shape of the object based on the pressure data; comparing the determined shape with a pre-stored shape of a human body to obtain a first similarity; and determining that the object is the person when the first similarity is greater than a first threshold.

When determining whether the object is the user, the method also includes acquiring pressure data from a plurality of points on the pad; determining a stressed area based on the pressure data; determining a density of the object based on a ratio of the pressure data to the stressed area; determining whether the density of the object is within a pre-stored range of densities of a human body; and determining that the object is the person when the density is within the pre-stored range of densities of the human body.

When determining the identity of the user, the method includes calculating difference values between a first set of physiological parameters and a second set of physiological parameters that are stored in a data list, wherein the first set of physiological parameters includes at least one of pressure data, stressed area, and density; selecting a target difference value in an allowable fluctuation range from the difference values, and determining a target physiological parameter from the second set of physiological parameters based on the target difference value; and acquiring the identity of the user based on the target physiological parameter, wherein the data list includes relationships between physiological parameters and identities of users.

The method also includes acquiring historical physiological parameters for each of a plurality of users in a first time period from a database; calculating an average of the historical physiological parameters of each of the plurality of users to obtain individualized sets of physiological parameters for the plurality of users; establishing relationships between the identities of the users and the individualized sets of physiological parameters by associating each of the identities of the users with a respective one of the individualized sets of physiological parameters; and generating the data list based on the relationships.

The method also includes acquiring an exercise parameter of the user within a first time period; comparing the exercise parameter with an upper exercise limit and a lower exercise limit of the user; and determining the allowable fluctuation range of the exercise parameter of the user based on a result of the comparison.

When determining the identity of the user, the method also includes acquiring biological characteristic information of the user, wherein the biological characteristic information includes at least one of fingerprint information, palm print information, and face information; comparing the acquired biological characteristic information with pre-stored biological characteristic information of at least one valid user; and accessing pre-stored identity information of the at least one valid user when a similarity between the acquired biological characteristic information and the pre-stored biological characteristic information of the at least one valid user is greater than a preset threshold.

When determining the identity of the user, the method also includes accessing account information of the user to log into a program on a terminal, and determining the identity of the user based on the account information.

When determining the at least one user preference, the method includes accessing historical watching information of the user in a first time period according to the identity of the user; and analyzing the historical watching information to acquire the at least one user preference of the user.

When determining the at least one user preference, the method also includes determining that a plurality of users are in contact with the pad; determining a sequence of contact by the plurality of users with the pad;

determining a plurality of user preferences corresponding to the plurality of users based on respective identities of each of the plurality of users; and sorting the plurality of user preferences based on the sequence of the contact to acquire a preference information list.

When transmitting the at least one instruction, the method includes establishing a wireless connection with the display device; and transmitting the at least one instruction including a booting instruction to the display device via the wireless connection.

Aspects of the disclosure also provide an apparatus. The apparatus includes a processor and a memory configured to store an instruction executable by the processor. The processor is configured to detect an object on a pad; determine whether the object is a user; determine an identity of the user when it is determined that the object is the user; determine at least one user preference associated with the user based on the identity of the user; and transmit, to the display device, at least one instruction to display information associated with the at least one user preference. The processor is also configured to determine that the user is a person.

The processor is also configured to calculate difference values between a first set of physiological parameters and a second set of physiological parameters that are stored in a data list, wherein the first set of physiological parameters includes at least one of the pressure data, stressed area, and density; select a target difference value in an allowable fluctuation range from the difference values, and determine a target physiological parameter from the second set of physiological parameters based on the target difference value; and acquire the identity of the user based on the target physiological parameter, wherein the data list includes relationships between physiological parameters and identities of users.

The processor is also configured to acquire historical physiological parameters for each of a plurality of users in a first time period from a database; calculate an average of the historical physiological parameters of each of the plurality of users to obtain individualized sets of physiological parameters for the plurality of users; establish relationships between the identities of the users and the individualized sets of physiological parameters by associating each of the identities of the users with a respective one of the individualized sets of physiological parameters; and generate the data list based on the relationships.

The processor is also configured to acquire biological characteristic information of the user, wherein the biological characteristic information includes at least one of fingerprint information, palm print information, and face information; compare the acquired biological characteristic information with pre-stored biological characteristic information of at least one valid user; and access pre-stored identity information of the at least one valid user when a similarity between the acquired biological characteristic information and the pre-stored biological characteristic information of the at least one valid user is greater than a preset threshold.

The processor is also configured to access account information of the user to log into a program on a terminal; and determine the identity of the user based on the account information.

Aspects of the disclosure also provide an apparatus. The apparatus includes a pad; a plurality of sensors uniformly arranged in a network pattern on the pad, wherein the sensors are configured to acquire data from the pad; and a transmitter configured to transmit the data to a terminal.

The sensors are configured to detect an object on the pad. The terminal is configured to determine whether the object is a user; determine an identity of the user when it is determined that the object is the user; determine at least one user preference associated with the user based on the identity of the user; and transmit, to the display device, at least one instruction to display information associated with the at least one user preference.

It is to be understood that both the foregoing general description and the following detailed description are only exemplary and are not restrictive of the present disclosure.

BRIEF DESCRIPTION OF THE DRAWINGS

The accompanying drawings here, which are incorporated into the specification and constitute a part of the specification, illustrate aspects consistent with the present disclosure, and together with the description, serve to explain the principles of the aspects of the present disclosure.

DETAILED DESCRIPTION

Reference will now be made in detail to exemplary aspects of the present disclosure, examples of which are illustrated in the accompanying drawings. The following description refers to the accompanying drawings in which the same numbers in different drawings represent the same or similar elements unless otherwise represented. The implementations set forth in the following description of exemplary aspects do not represent all implementations consistent with the disclosure. Instead, they are merely examples of apparatuses and methods consistent with aspects related to the disclosure as recited in the appended claims.

Certain terms used in the present disclosure are only intended to describe specific aspects, but are not intended to limit the present disclosure. For example, singular form words "a," "said," and "the" used in the present disclosure and the appended claims are intended to include plural form, unless otherwise clearly stated. Also, the term "and/or" used herein refers to any or all combinations of one or more listed related items.

It is to be understood that although the aspects of the present disclosure may apply terms including first, second, third and so on to describe various information, these information should not be limited to these terms. These terms are only used for distinguishing information of the same type from each other. For example, first information may be also called second information without departing from the scope of the aspects of the present disclosure, and similarly, second information may be also called first information, which depends on context. For example, the word "if" used here may be interpreted as "at the moment when . . . " or "when . . . " or "in response to confirmation".

Figure 1A:
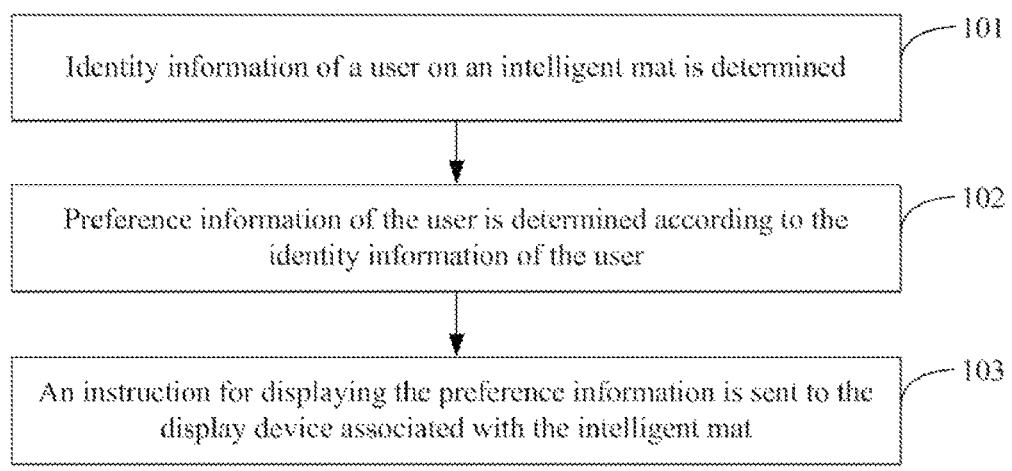
FIG. 1A is a flowchart of a method for controlling a display device according to an exemplary aspect of the present disclosure.

As shown in FIG. 1A, FIG. 1A is a flowchart of a method for controlling a display device according to an exemplary aspect. The method may be applied to a terminal, and may be also applied to an intelligent pad. The present aspect illustrates application of the method to a terminal as an example. The method may include the following steps.

Step 101: Identity information of a user on an intelligent pad is determined.

The terminal in the present disclosure may be any intelligent terminal having an Internet access function. For example, the terminal may be a smart phone, a tablet computer, a Personal Digital Assistant (PDA) and so on, wherein the terminal may access a router by a wireless local area network, and access a server in a public network through the router. An Application (App) is installed on the terminal, and a display device associated with the intelligent pad may be controlled by the App. A network communication module capable of communicating with the terminal is provided in the intelligent pad and the display device. The intelligent pad in the aspects of the present disclosure may include a mattress, a seat cushion, a sofa cushion and so on, and the aspects of the present disclosure mainly illustrate a mattress as an example.

The step of the aspects of the present disclosure aims to determine that an object on the intelligent pad is a user (i.e., a person), but not an animal or another object, such as a pillow, a quilt and so on. For example, when a user lies on a mattress or sits on a sofa cushion, it may be first detected whether the object on the intelligent pad is a user, and when a user is detected, identity information of the user is determined.

Several temperature sensors may be arranged on the intelligent pad in the aspects of the present disclosure, and several pressure sensors may be also arranged thereon. The temperature sensors and the pressure sensors may be arranged uniformly in a network pattern on the intelligent pad. The temperature sensors are configured to detect the temperature of the object on the intelligent mat, and the pressure sensors are configured to detect a received pressure. Each pressure sensor corresponds to a detection point.

In the step of the aspects of the present disclosure, whether the object on the intelligent pad is a user may be detected by one or more of the following manners.

Manner 1

The terminal uses the pressure sensors arranged on the intelligent pad to acquire pressure information on the intelligent mat, and determines the shape of the object on the intelligent pad according to points where the pressure information is capable of being acquired on the intelligent pad. In an aspect of the present disclosure, the shape may be determined based on detection points of the outermost circle among detection points that the pressure information is capable of being acquired, the determined shape is compared with a pre-stored shape of a human body, so as to obtain a first similarity, and if the first similarity is larger than a first preset threshold, it is determined that the object is a user, and otherwise, it is determined that the object is another object. The shape of the human body here may be the shape of the whole human body, or may be also the shape of a part of the human body, because for a seat cushion, an acquired shape is the shape of the buttocks and legs corresponding to the user sitting on the seat cushion.

In the manner of the pressure information on the intelligent pad present disclosure, the shape of the object on the intelligent pad is determined according to the pressure information, and whether the object is a user is judged according to the shape, thereby improving the judgment efficiency.

Manner 2

The terminal uses the pressure sensors to acquire pressure information on the intelligent pad and determines a stressed area according to points where the pressure information is capable of being acquired on the intelligent mat, then calculates the ratio of the pressure information to the stressed area so as to obtain the density of the object on the intelligent mat, then compares the density of the objet with a pre-stored range of human body density, and if the calculated density is in the pre-stored range of human body density, then determines that the object is a user, and otherwise, determines that the object is other object.

In the manner of the aspects of the present disclosure, whether the object on the intelligent pad is a user is judged according to density. Since the density of a human body is significantly different from the density of other objects, the judgment accuracy can be improved.

Further, the pre-stored range of human body density may be determined according to history data. For example, pressure information and a stressed area on a mattress where a user lies on his/her back are acquired from history data, and a range of human body density of a human body lying on his/her back is acquired according to the ratio of the pressure information to the stressed area. Pressure information and a stressed area of a mattress on which a user sits may be also acquired from history data, so as to acquire a range of human density of a sitting human body.

Manner 3

The terminal uses the temperature sensors to acquire temperature data of the object on the intelligent mat, compares the acquired temperature data with a pre-stored range of human body temperature, and if the temperature data is in the pre-stored range of human body temperature, determines that the object on the intelligent pad is a user, and otherwise, determines that the object on the intelligent pad is other object, but not a human body. In the step of the aspects of the present disclosure, since various parts of a human body have roughly the same temperature, temperature data acquired by only some temperature sensors may be compared with the range of human body temperature. Some temperature data may be compared with the range of human body temperature respectively. The temperature data may be also calculated to acquire an average value and the average value is compared with the range of human body temperature. Or the acquired temperature data is calculated based on some other algorithms to obtain a reference temperature value that can reflect the overall temperature data, and the reference temperature value acquired through the calculation is compared with the range of human body temperature.

In the method of the aspects of the present disclosure, whether the object is a user is judged according to temperature, thereby improving the judgment efficiency.

It is to be understood that manners for detecting whether an object on the intelligent pad is a user are not limited to the manners above, which may be manners for determining a user in the related art. Besides, whether the object is a user may be judged by one manner so as to improve the judgment efficiency, or may be also judged by combining a plurality of manners, so as to improve the judgment accuracy. For example, the judgment is performed by combining the first manner and the second manner, or by combining the first manner and the third manner, and so on.

Subsequently, the identity information of the user may be determined.

A plurality of users may use the intelligent pad in a family, and the users who use the intelligent pad may be called valid users, thus identity information of each valid user may be pre-stored in the terminal, such as information that can identify the user, including a name, a username, an account, a body height, a body weight, face image information and a mobile phone number and so on. The identity information of the user may be determined by the following modes.

Mode 1: The identity information of the user is determined according to physiological parameters.

First, difference values between physiological parameters and sample physiological parameters in a data list are calculated.

The physiological parameters may include pressure information, stressed area, the density of a user, and the height of the user and so on. When the physiological parameters are information (such as pressure information, stressed area, and the density of a user) acquired during the process of determining a user, the physiological parameters may be acquired directly, otherwise, the physiological parameters need to be acquired separately. For example, for an intelligent mattress, the terminal may determine the body length (body height) of a user lying on the intelligent mattress based on points that are the farthest from each other in the length direction of the intelligent mattress. The length direction of the intelligent pad is the direction of the body height of a human body lying thereon, and generally, points that are the farthest to each other in this direction are the positions of the head and the feet, thus the approximate height of the user may be determined by this mode. The data list records corresponding relations between sample physiological parameters and identity information of users. Different sample physiological parameters correspond to different valid users, thus the identity of a corresponding user may be determined according to sample physiological parameters.

Secondly, the difference values are compared with an allowable fluctuation range, a target difference value in the allowable fluctuation range is selected from the difference values, and a target sample physiological parameter corresponding to the target difference value is determined. The identity information of a user corresponding to the target sample physiological parameter is acquired from the data list. A physiological parameter of a user may change as time goes by, a body weight may change, for example, thereby resulting in a change in pressure information and a stressed area; therefore, physiological parameters corresponding to difference values in the allowable fluctuation range may be the same user.

It may be understood that the identity of the user may be determined by one type of physiological parameter, and the identity of the user may be also determined by combining a plurality of physiological parameters so as to improve the accuracy in recognizing the identity. For example, the identity is recognized by combining the pressure information and the stressed area. When the pressure information and sample pressure information are in an allowable fluctuation range, and when the stressed area and a sample stressed area are in an allowable fluctuation range, the corresponding identity information is determined.

For example, pressure information on the intelligent pad is acquired, a stressed area is determined based on points where the pressure information can be acquired on the intelligent mat, a pressure difference value between the pressure information and sample pressure information in the data list is calculated, an area difference value between the stressed area and a sample stressed area in the data list is calculated, wherein the data list records corresponding relations among sample pressure information, sample stressed areas and identity information of users, a group of target sample pressure information and target sample stressed areas having a pressure difference value and an area difference value within allowable fluctuation ranges is selected, and identity information of a user corresponding to the target sample pressure information and the target sample stressed area is determined according to the data list.

Further, a manner for creating the data list may include the followings.

Firstly, history physiological parameters of each user in a first history period are acquired from a database. The first history period is a preset recent period of time. For example, the first history period may be recent one week, or recent one month, which may be specifically set as required. Current physical conditions of the user may be truly reflected by acquiring history physiological parameters within a recent period of time, thereby improving the reliability of the sample physiological parameters in the data list.

Secondly, history physiological parameters of each user are averaged to obtain sample physiological parameters of the each user. Each user corresponds to a plurality of history physiological parameters, and physical conditions of each user may be reflected comprehensively by averaging physiological parameters of the each user, thereby improving the reliability of the sample physiological parameters in the data list.

Finally, corresponding relations between identity information of users and sample physiological parameters are created and the data list is obtained.

The identity information of the user may be determined according sample physiological parameters by creating the corresponding relations between the identity information of users and the sample physiological parameters.

Further, the allowable fluctuation range may be also determined.

In an alternative implementation mode, the allowable fluctuation range may be determined by the following way.

Firstly, an exercise parameter of the user within a second history period is acquired. The second history period is a preset recent period of time. For example, the second history period may be the recent one week, or the recent one month, which may be specifically set as required. The second history period may be the same as a first period, or may be also different. In the present step, the exercise parameter of the user may be acquired by a portable device associated with the terminal. For example, an exercise parameter of the user in the recent one week may be acquired through a smart wrist band.

Secondly, the exercise parameter is compared with an upper exercise limit and a lower exercise limit of the user.

Finally, the allowable fluctuation range of the exercise parameter of the user is determined according to a comparison result.

The upper exercise limit and the lower exercise limit of the user may be preset. The values may be used for measuring a possible changing trend of physiological parameters. For example, when the exercise parameter is larger than the upper exercise limit, it is considered that there is a large amount of exercise, which may result in a decrease in the pressure information and the stressed area, and the allowable fluctuation range may be decreased at the moment. When the exercise parameter is smaller than the lower exercise limit, it is considered that there is a small amount of exercise, which may result in an increase in the pressure information and the stressed area, and the allowable fluctuation range may be increased at the moment. Thus, the allowable fluctuation range of the exercise parameter of the user may be determined according to a comparison result, wherein a specific value of the fluctuation range may be designated.

For example, provided that a default allowable fluctuation range is ($-10\%$ $w_0$,$+10°$ % $w_0$), the allowable fluctuation range may be increased if a user has an extremely small exercise amount recently according to an exercise amount recorded by a wrist band in the recent one week of the user. For example, the fluctuation range of pressure information (W) is increased to ($-10\%$ $w_0$,$+20\%$ $w_0$) or the allowable fluctuation range may be reduced, to ($-20\%$ $w_0$,$+10\%$ $w_0$), for example, if the user has an extremely large exercise amount recently, wherein $w_0$ is a sample pressure parameter corresponding to the user.

The way adjusts the allowable fluctuation range according to the exercise parameter, which considers the factor that a physiological parameter changes with the exercise parameter, thereby improving the accuracy in determining the identity information.

In another alternative implementation mode, a fluctuation range may be preset. The fluctuation range may be a proportion, and may be also a specific value. For example, a fluctuation range of the pressure information may be fixed at ($-10\%$ $w_0$,$+10\%$ $w_0$), wherein $w_0$ is a sample pressure parameter corresponding to the user. For another example, a fluctuation range of the pressure information is set as ($-5$ kg,$+5$ kg).

Mode 2: The identity information of the user is determined according to biologic characteristic information.

Firstly, biologic characteristic information of the user is acquired. The biologic characteristic information may include fingerprint information, palm print information, face information and so on. For example, the terminal may recognize the face of the user by a built-in camera, or may also recognize the fingerprint of the user by a built-in fingerprint recognition module.

Secondly, the acquired biologic characteristic information is compared with pre-stored biologic characteristic information of at least one valid user.

Biologic characteristic information may have little change as time progresses, thus the acquired biologic characteristic information may be directly compared with pre-stored biologic characteristic information of a valid user.

Finally, when a second similarity of the acquired biologic characteristic information to biologic characteristic information of a valid user is larger than a second preset threshold, pre-stored identity information of the valid user is read.

When the acquired biologic characteristic information is similar to biologic characteristic information of a valid user, it may be determined that the object on the intelligent pad is the valid user, thus identity information of the valid user is determined to be identity information of the object.

In an aspect of the present disclosure, biologic characteristic information and corresponding identity information of each valid user are pre-stored in the terminal. After a user currently located on the intelligent pad is determined according to biologic characteristic information, corresponding identity information may be read from a database.

Mode 3: The identity information of the user is determined according to account information used by the user to log in an App on the terminal.

Account information used by the user to log in an App on the terminal is read. Before using the intelligent mat, the user may log in any App on the terminal, and account information for logging in the App may be acquired to determine the identity information of the user according to the account information. On one hand, the account information may be determined as the identity information directly. In other words, the identity information exists in a form of account information. On the other hand, the identity information may be also determined according to a pre-created relation between the account information and the identity information. For example, the account information is an account, and the identity information is a name, then a relation between the account and the name is created in advance. After the account is acquired, the corresponding name may be determined according to the account so as to acquire the name of the user.

Step 102: Preference information of the user is determined according to the identity information of the user.

In the step of the aspects of the present disclosure, the preference information may include an audio, a video, an image, a webpage, an electronic book and so on.

In an alternative implementation mode, history watching information of the user in a third history period may be read according to the identity information of the user, and the history watching information is analyzed to acquire the preference information of the user, wherein the third history period is a preset recent period of time. For example, the third history period may be the recent one week, or the recent one month, which may be specifically set as required. The third history period may be the same as the first history period or the second history period, or may be also different from the first history period or the second history period.

A preset strategy may be applied when the history watching information is analyzed. For example, information that is not completely played by the user before shutdown has the highest priority. For example, the user performs shutdown without finishing playing a movie "XXX" when watching the movie last time, then the playing progress of the movie may be acquired this time to continue playing the movie "XXX". On the other hand, weights of the information may be also determined according to playing frequencies of the information so as to determine a playing sequence of the information according to the weights. For example, it is analyzed according to statistics of the history watching information that the user likes to watch American television series, and then the preference information is American television series. For another example, it is analyzed according to statistics of the history watching information that, within one week, the user watched a television play A for 5 times, watched a television play B for 6 times, watched a television play C for 3 times, browsed a webpage D twice, and read an electronic book E for 7 times, then the preference information is: the electronic book E, the television play B, the television play A, the television play C and the webpage D.

In another alternative implementation mode, when there are at least two users on the intelligent mat, a sequence that the at least two users contact the intelligent pad is acquired; preference information corresponding to each of the at least two users is determined according to identity information of the at least two users; the preference information is sorted according to the sequence to acquire a preference information list. The present aspect illustrates the situation where there is a plurality of users on the intelligent pad. Each user corresponds to preference information, the users may be sorted according to a sequence of contact with the intelligent mat, and preference information corresponding to the users is further sorted, thus preference information of a user who contacts the intelligent pad first will be displayed first.

Step 103: An instruction for displaying the preference information is sent to a display device associated with the intelligent pad.

The present step may send an instruction for displaying the preference information to a display device associated with the intelligent pad so that the display device can display the preference information. The display device may be a television, a large screen display, a projector and so on. The display device may locally acquire, according to the instruction, data corresponding to the preference information, may also acquire data corresponding to the preference information from a could, and may also acquire data corresponding to the preference information from a terminal. For example, the display device may acquire data corresponding to the preference information from a terminal, including a mobile phone, a tablet computer, a laptop computer and so on of the user.

In an alternative implementation mode, the instruction for displaying the preference information may be an instruction for directly displaying data corresponding to the preference information. For example, when there is a plurality of pieces of preference information, specific data corresponding to the preference information may be displayed in turn. For example, American television series A may be played first according to the preference information, American television series B are played when a switching instruction is received or a preset moment arrives, and so on.

Figure 1B:
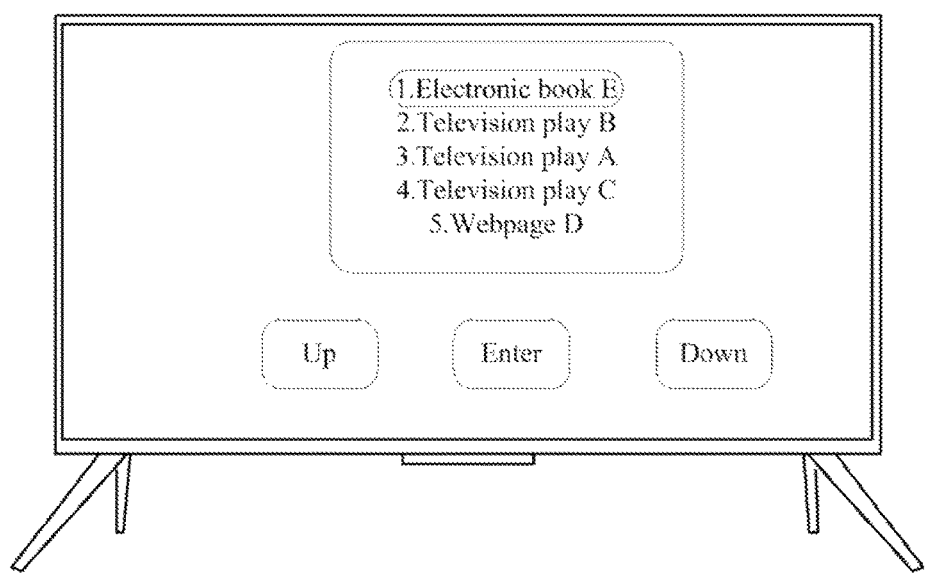
FIG. 1B is a schematic diagram of displaying preference information according to an exemplary aspect of the present disclosure.

In another alternative implementation mode, the instruction for displaying the preference information may be an instruction for displaying the preference information list. For example, FIG. 1B shows a schematic diagram of displaying preference information according to an exemplary aspect of the present disclosure. A prompt box pops up on the display device, and a preference information list "electronic book E, television play B, television play A, television play C and webpage D" is displayed in the prompt box. The user may select corresponding information by touch, gesture control, eyeball control and so on. For example, the user touches a control button on the desktop of the terminal to select "up", "down" or "enter".

Further, a wireless connection with the display device associated with the intelligent pad may be created; and then a booting instruction and the instruction for displaying the preference information are sent to the display device through the wireless connection, so as to implement automatic booting and display the preference information.

It may be seen from the foregoing aspects that the aspects of the present disclosure determine identity information of a user on an intelligent mat, determines preference information of the user according to the identity information of the user, and then sends an instruction for displaying the preference information to a display device associated with the intelligent mat, so that the preference information of the user on the intelligent pad can be displayed and the user does not need to select the preference information manually from a large amount of data, thus improving searching efficiency and bringing more use convenience for the user.

It is to be noted that the method may be also applied to an intelligent pad besides a terminal. The intelligent pad determines identity information of a user on the mat, determines preference information of the user according to the identity information of the user, and then sends an instruction for displaying the preference information to a display device associated with the intelligent pad. A specific implementation method is similar to the aspects above, and will not be described repeatedly in details here.

In an alternative implementation mode, when the display device is a projector, the method further includes that: a posture of the user on the intelligent pad is determined according to the stressed area and pre-stored corresponding relations between stressed areas and postures, wherein the posture may include a sitting posture, a supine position and so on, a projection direction of the projector is determined according to the determined posture and pre-stored corresponding relations between pre-stored projection directions and postures; and then the projection direction is sent to the projector associated with the intelligent mat, thus controlling a direction of the projector automatically and improving user experience.

In an alternative implementation mode, when the identity information of the user cannot be recognized, information on the top of a recent playing list may be played or recommended, or playing of the content played last time is continued by default.

Figure 2:
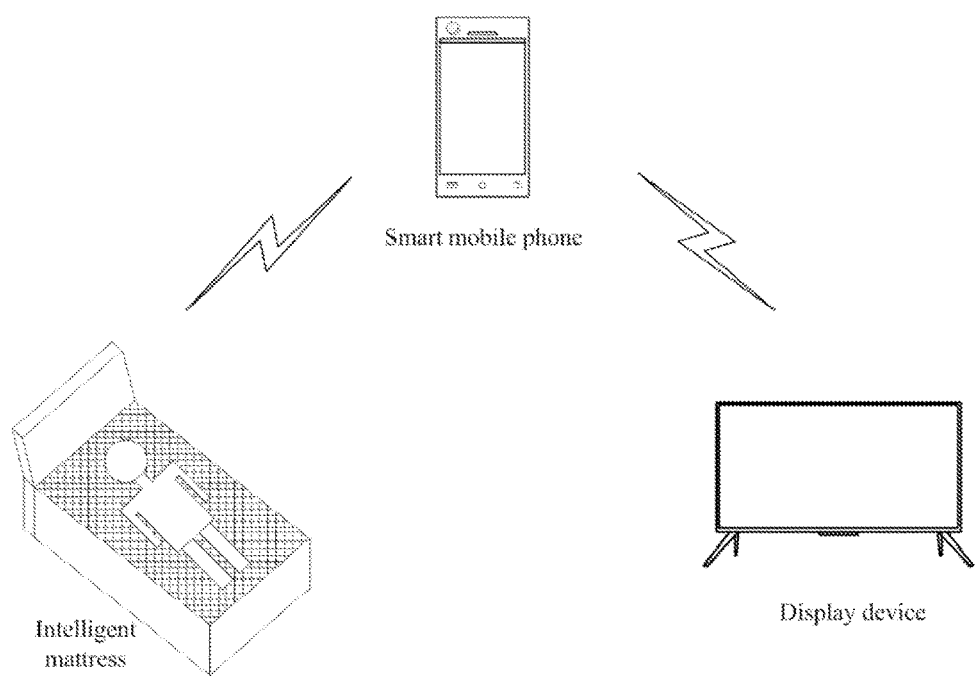
FIG. 2 is a schematic diagram of an application scenario of a method for controlling a display device according to an exemplary aspect of the present disclosure.

As shown in FIG. 2, FIG. 2 is a schematic diagram of an application scenario of a method for controlling a display device according to an exemplary aspect of the present disclosure. The scenario as shown in FIG. 2 includes: a smart phone functioning as a terminal, an intelligent mat, and a display device associated with the intelligent pad. A user lies on the intelligent mattress. Several pressure sensors and temperature sensors are arranged on the intelligent mattress, which are the intersections of the network in FIG. 2. A network communication module capable of communicating with the smart phone is provided in the intelligent mattress. A network communication module capable of communicating with the smart phone is also provided in the display device.

The terminal controls the pressure sensors on the intelligent mattress to acquire pressure information, the shape of an object on the intelligent pad is determined according to points where the pressure information can be acquired on the intelligent mat, the shape is compared with a pre-stored shape of a human body to determine that the object lying on the mattress is a user, then the terminal reads network account information used by the user to log in an App, and pre-stored identity information of the user is read based on the network account information, and preference information of the user is determined according to the identity information of the user, and an instruction for displaying the preference information is sent to the display device associated with the intelligent mat, thus displaying the preference information automatically and improving the efficiency in acquiring the preference information.

In the application scenario as shown in FIG. 2, a specific process for controlling the display device may refer to the description of FIG. 1A, and will not be described repeatedly here.

Corresponding to the aspects of the method for controlling the display device, the aspects of the present disclosure further provide aspects of an apparatus for controlling a display device, an apparatus and an intelligent pad.

Figure 3:
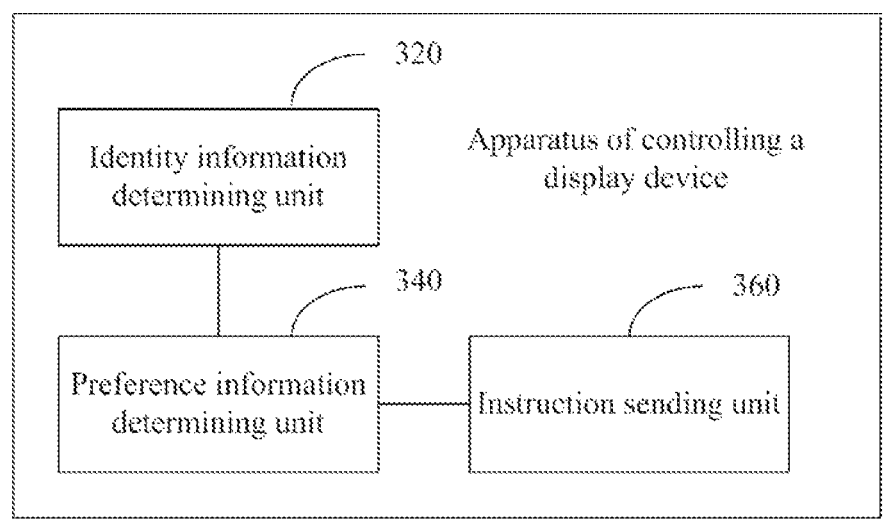
FIG. 3 to FIG. 15 show block diagrams of an apparatus for controlling a display device according to an exemplary aspect of the present disclosure.

As shown in FIG. 3, FIG. 3 is a block diagram of an apparatus for controlling a display device according to an exemplary aspect of the present disclosure. The apparatus includes: an identity information determining unit 320, a preference information determining unit 340 and an instruction sending unit 360.

The identity information determining unit 320 is configured to determine identity information of a user on an intelligent mat;

the preference information determining unit 340 is configured to determine preference information of the user according to the identity information of the user; and the instruction sending unit 360 is configured to send an instruction for displaying the preference information to a display device associated with the intelligent pad.

It may be seen from the aspect above that the aspect of the present disclosure determines identity information of a user on an intelligent mat, determines preference information of the user according to the identity information of the user, and then sends an instruction for displaying the preference information to a display device associated with the intelligent mat, so that the preference information of the user on the intelligent pad is displayed and the user does not need to select the preference information manually from a large amount of data, thus improving searching efficiency and bringing more use convenience for the user.

Figure 4:
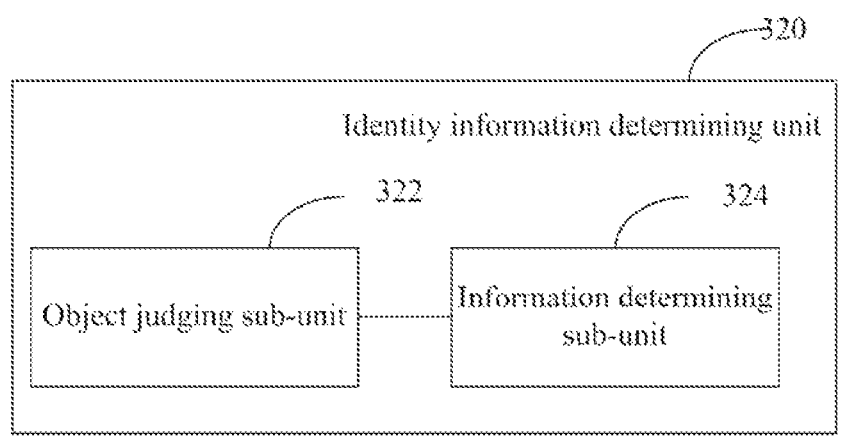

As shown in FIG. 4, FIG. 4 is a block diagram of another apparatus for controlling a display device according to an exemplary aspect of the present disclosure. The aspect is based on the aspect as shown in FIG. 3, the identity information determining unit 320 includes an object judging sub-unit 322 and an information determining sub-unit 324.

The object judging sub-unit 322 is configured to detect whether an object on the intelligent pad is a user; and the information determining sub-unit 324 is configured to determine, when a user is detected, identity information of the user.

It may be seen from the aspect above that the aspect of the present disclosure first determines whether an object on the intelligent pad is a user, and when the object is a user, determines identity information of the user, so that other objects which are not human bodies are filtered, only a user is identified to determine identity information, thus improving the efficiency in determining identity information.

Figure 5:
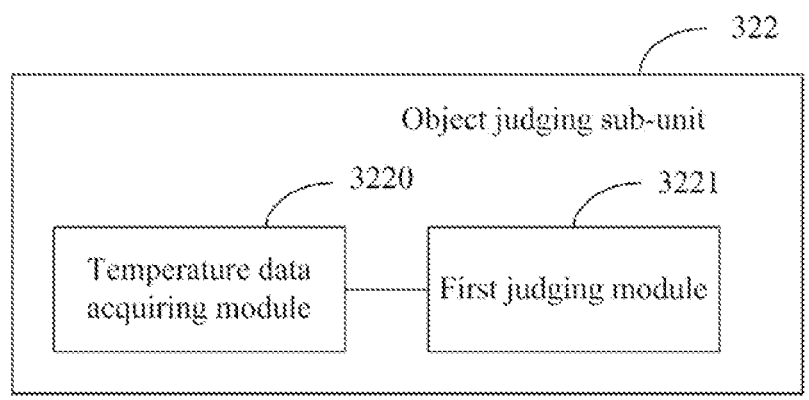

As shown in FIG. 5, FIG. 5 is a block diagram of still another apparatus for controlling a display device according to an exemplary aspect of the present disclosure. The aspect is based on the aspect as shown in FIG. 4, the object judging sub-unit 322 includes a temperature data acquiring module 3220 and a first judging module 3221.

The temperature data acquiring module 3220 is configured to acquire temperature data of the object on the intelligent mat; and the first judging module 3221 is configured to determine that the object on the intelligent pad is a user when the temperature data is in a pre-stored range of human body temperature.

It may be seen from the aspect above that, in the aspect of the present disclosure, temperature data of the object on the intelligent pad is acquired and compared with a pre-stored range of human body temperature, and the object is determined to be a user only when the temperature data is in the pre-stored range of human body temperature, thereby improving the judgment efficiency.

Figure 6:
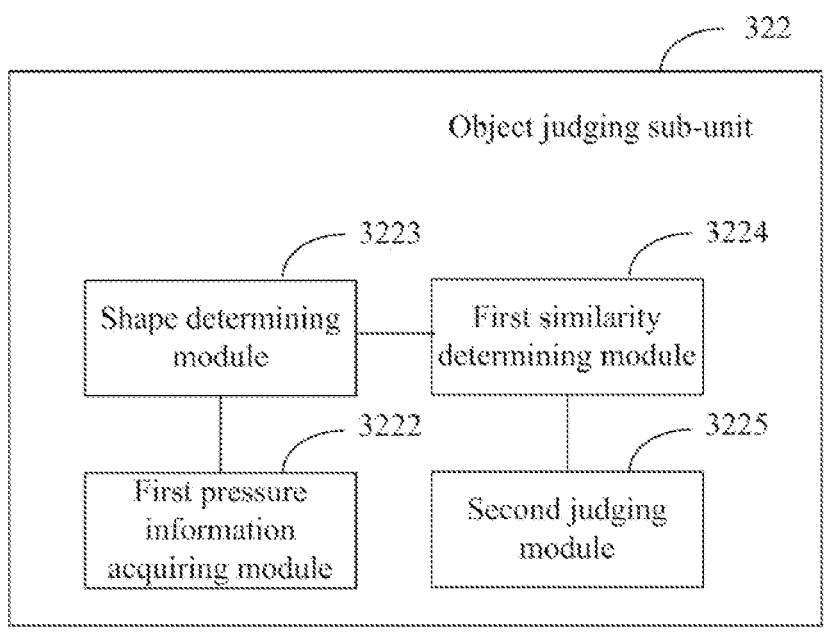

As shown in FIG. 6, FIG. 6 is a block diagram of still another apparatus for controlling a display device according to an exemplary aspect of the present disclosure. The aspect is based on the aspect as shown in FIG. 4, the object judging sub-unit 322 includes a first pressure information acquiring module 3222, a shape determining module 3223, a first similarity determining module 3224 and a second judging module 3225.

The first pressure information acquiring module 3222 is configured to acquire pressure information on the intelligent mat;

the shape determining module 3223 is configured to determine the shape of the object on the intelligent pad according to points where the pressure information can be acquired on the intelligent mat:

the first similarity determining module 3224 is configured to compare the determined shape with a pre-stored shape of a human body, so as to obtain a first similarity; and the second judging module 3225 is configured to determine that the object is a user when the first similarity is larger than a first preset threshold.

It may be seen from the aspect above that, in the aspect of the present disclosure, pressure information on the intelligent pad is acquired, and the shape of the object on the intelligent pad is determined according to points where the pressure information can be acquired on the intelligent mat, so that the determined shape can be compared with a pre-stored shape of a human body to judge whether the object on the intelligent pad is a user, thus improving the judgment efficiency.

Figure 7:
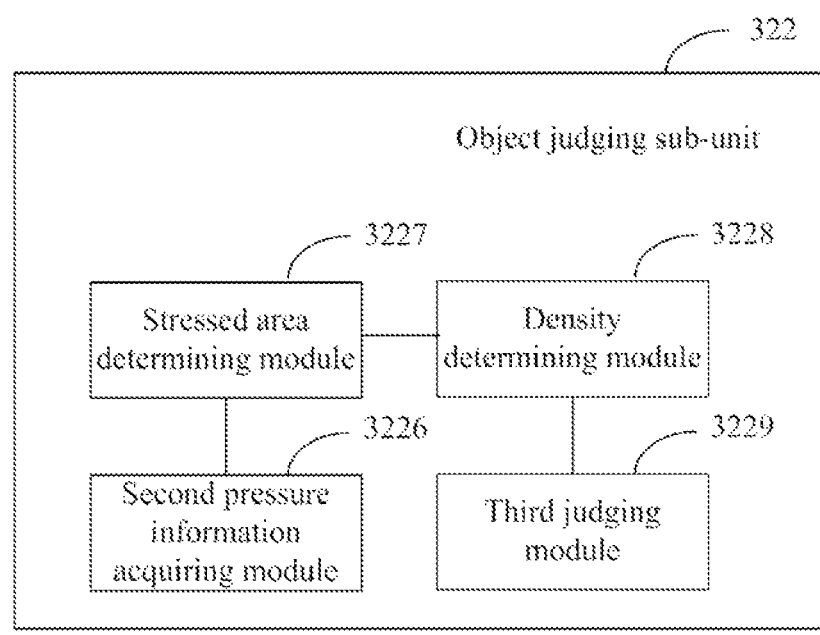

As shown in FIG. 7, FIG. 7 is a block diagram of still another apparatus for controlling a display device according to an exemplary aspect of the present disclosure. The aspect is based on the aspect as shown in FIG. 4, the object judging sub-unit 322 includes a second pressure information acquiring module 3226, a stressed area determining module 3227, a density determining module 3228 and a third judging module 3229.

The second pressure information acquiring module 3226 is configured to acquire pressure information on the intelligent mat;

the stressed area determining module 3227 is configured to determine a stressed area according to points where the pressure information can be acquired on the intelligent mat;

the density determining module 3228 is configured to calculate the ratio of the pressure information to the stressed area to obtain the density of the object on the intelligent mat; and the third judging module 3229 is configured to determine that the object is a user when the calculated density is in a pre-stored range of human body density.

It may be seen from the aspect above that, in the aspect of the present disclosure, pressure information on the intelligent pad is acquired, a stressed area is determined according to points where the pressure information can be acquired on the intelligent mat, the ratio of the pressure information to the stressed area is calculated so as to obtain the density of the object on the intelligent mat, and the object is determined to be a user when the calculated density is in a pre-stored range of human body density. Whether the object on the intelligent pad is a user is determined according to the density, thus improving the judgment accuracy.

Figure 8:
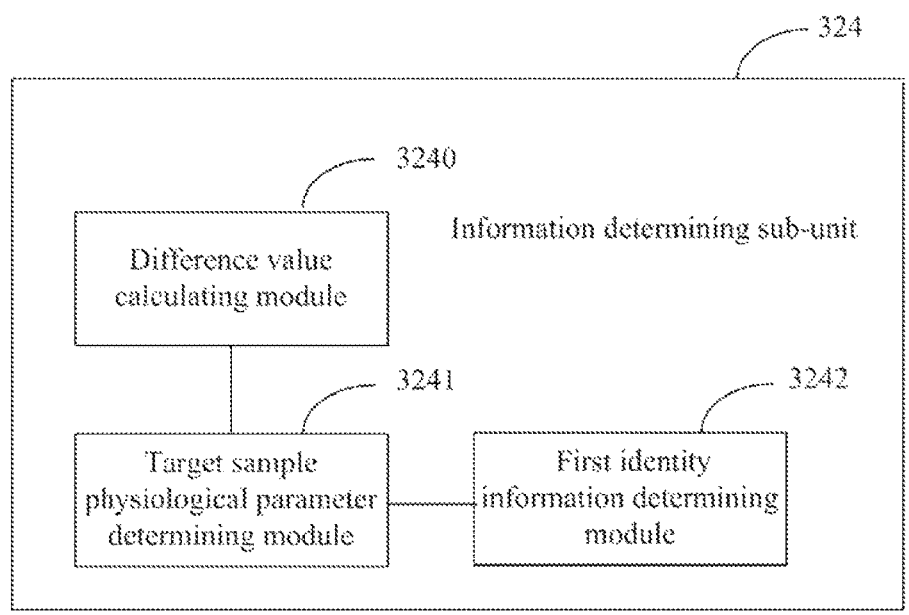

As shown in FIG. 8, FIG. 8 is a block diagram of still another apparatus for controlling a display device according to an exemplary aspect of the present disclosure. The aspect is based on the aspect as shown in FIG. 7, the information determining sub-unit 324 includes a difference value calculating module 3240, a target sample physiological parameter determining module 3241, and a first identity information determining module 3242.

The difference value calculating module 3240 is configured to calculate difference values between physiological parameters and sample physiological parameters in a data list, wherein the physiological parameters include the pressure information, the stressed area or the density;

the target sample physiological parameter determining module 3241 is configured to select a target difference value in an allowable fluctuation range from the difference values, and determine a target sample physiological parameter corresponding to the target difference value; and the first identity information determining module 3242 is configured to acquire identity information of a user corresponding to the target sample physiological parameter from the data list, wherein the data list records corresponding relations between sample physiological parameters and identity information of users.

It may be seen from the aspect above that, in the aspect of the present disclosure, difference values between physiological parameters and sample physiological parameters in a data list are calculated, a target difference value in an allowable fluctuation range is selected from the difference values, so as to determine the identity information of the user, thus determining the identity information according to the physiological parameters. Since the physiological parameters have been determined when the user is determined, it is unnecessary to acquire other data when the identity information is determined, thus saving resources.

Figure 9:
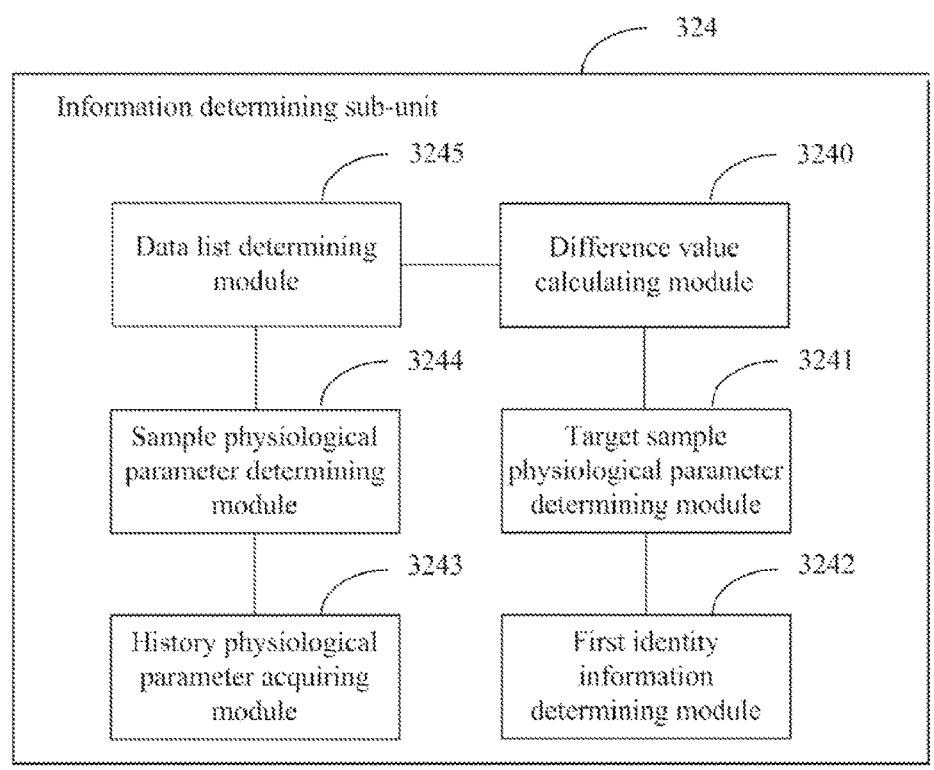

As shown in FIG. 9, FIG. 9 is a block diagram of still another apparatus for controlling a display device according to an exemplary aspect of the present disclosure. The aspect is based on the aspect as shown in FIG. 8, the information determining sub-unit 324 further includes a history physiological parameter acquiring module 3243, a sample physiological parameter determining module 3244 and a data list determining module 3245.

The history physiological parameter acquiring module 3243 is configured to acquire history physiological parameters of each user in a first history period from a database;

the sample physiological parameter determining module 3244 is configured to average the history physiological parameters of the each user to obtain sample physiological parameters of the each user; and the data list determining module 3245 is configured to create corresponding relations between identity information of users and sample physiological parameters and obtain the data list.

It may be seen from the aspect above that, in the aspect of the present disclosure, history physiological parameters are averaged to obtain sample physiological parameters and corresponding relations between identity information of users and sample physiological parameters are created so as to obtain the data list, thereby improving the reliability of the sample physiological parameters.

Figure 10:
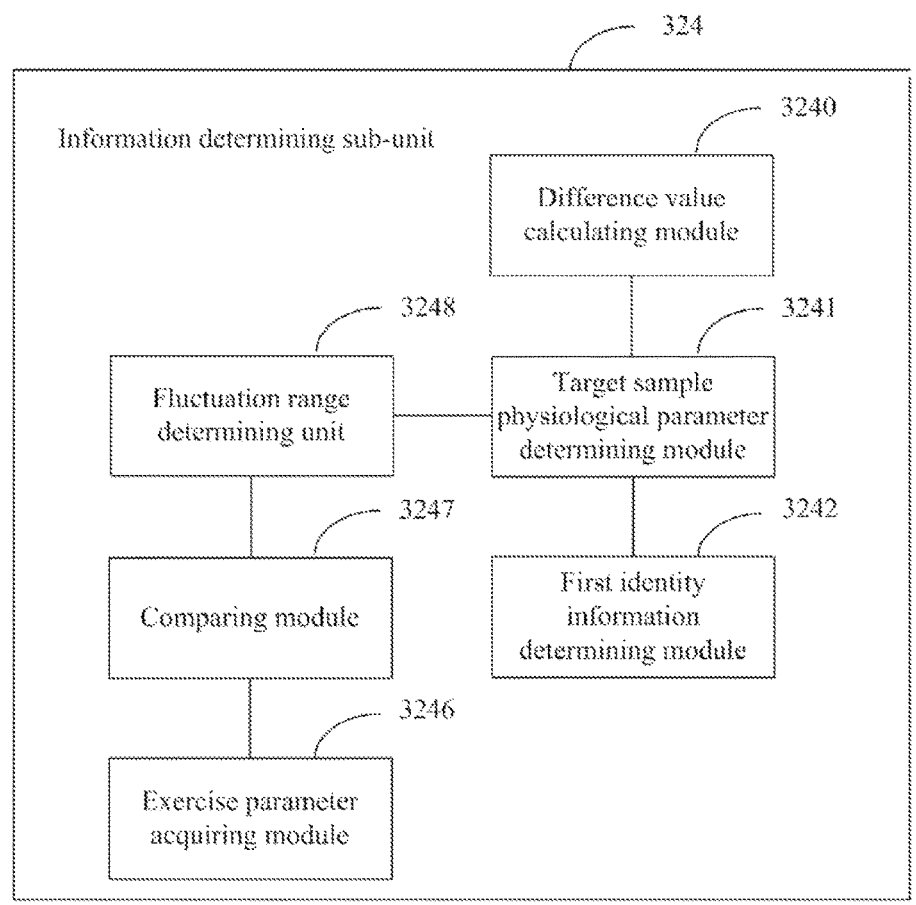

As shown in FIG. 10, FIG. 10 is a block diagram of still another apparatus for controlling a display device according to an exemplary aspect of the present disclosure. The aspect is based on the aspect as shown in FIG. 8, the information determining sub-unit 324 further includes an exercise parameter acquiring module 3246, a comparing module 3247 and a fluctuation range determining unit 3248.

The exercise parameter acquiring module 3246 is configured to acquire an exercise parameter of the user within a second history period;

the comparing module 3247 is configured to compare the exercise parameter with an upper exercise limit and a lower exercise limit of the user; and the fluctuation range determining unit 3248 is configured to determine an allowable fluctuation range of the exercise parameter of the user according to a comparison result.

It may be seen from the aspect above that, in the aspect of the present disclosure, an exercise parameter of the user within a second history period is acquired, the exercise parameter is compared with an upper exercise limit and a lower exercise limit of the user; and an allowable fluctuation range of the exercise parameter of the user is determined according to a comparison result. The allowable fluctuation range is adjusted according to the exercise parameter, which considers a factor that the physiological parameters change with the exercise parameter, thereby improving the accuracy of the allowable fluctuation range and further improving the accuracy in determining the identity information.

Figure 11:
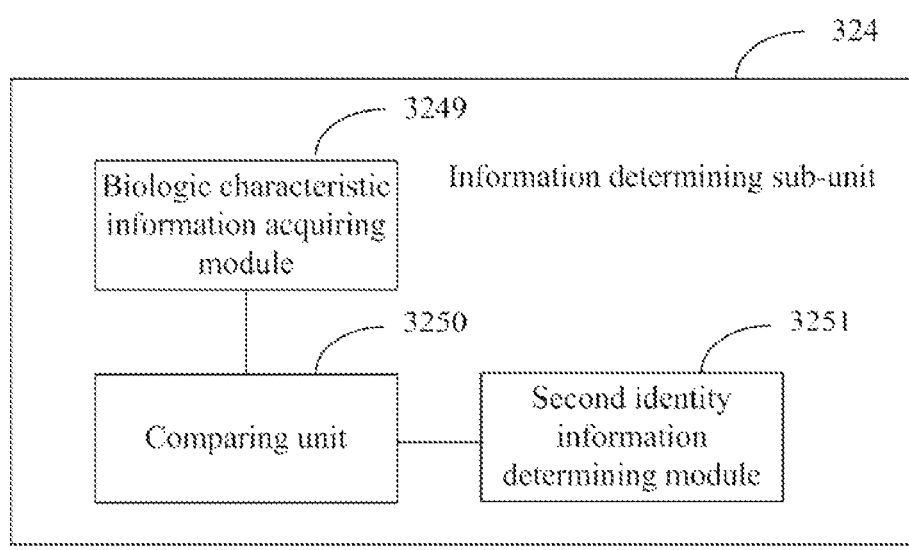

As shown in FIG. 11, FIG. 11 is a block diagram of still another apparatus for controlling a display device according to an exemplary aspect of the present disclosure. The aspect is based on the aspect as shown in FIG. 4, the information determining sub-unit 324 includes a biologic characteristic information acquiring module 3249, a comparing unit 3250 and a second identity information determining module 3251.

The biologic characteristic information acquiring module 3249 is configured to acquire biologic characteristic information of the user, wherein the biologic characteristic information includes fingerprint information, palm print information and face information;

the comparing unit 3250 is configured to compare the acquired biologic characteristic information with pre-stored biologic characteristic information of at least one valid user; and the second identity information determining module 3251 is configured to read, when a second similarity of the acquired biologic characteristic information to biologic characteristic information of a valid user is larger than a second preset threshold, pre-stored identity information of the valid user.

It may be seen from the aspect above that, in the aspect of the present disclosure, the identity information of the user is determined by comparing acquired biologic characteristic information with pre-stored biologic characteristic information of a valid user, thereby improving the determining accuracy.

Figure 12:
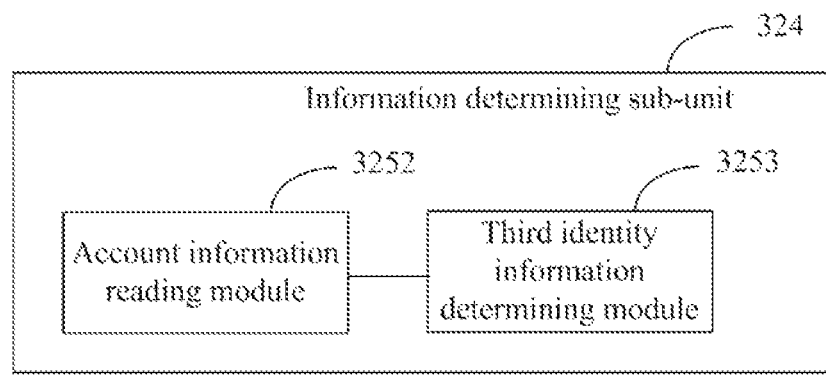

As shown in FIG. 12, FIG. 12 is a block diagram of still another apparatus for controlling a display device according to an exemplary aspect of the present disclosure. The aspect is based on the aspect as shown in FIG. 4, the information determining sub-unit 324 includes an account information reading module 3252 and a third identity information determining module 3253.

The account information reading module 3252 is configured to read account information used by the user to log in an App on a terminal; and the third identity information determining module 3253 is configured to determine the identity information of the user according to the account information.

It may be seen from the aspect above that, in the aspect of the present disclosure, account information used by the user to log in an App on a terminal is read; and the identity information of the user is determined according to the account information, thereby improving the determining efficiency and accuracy.

Figure 13:
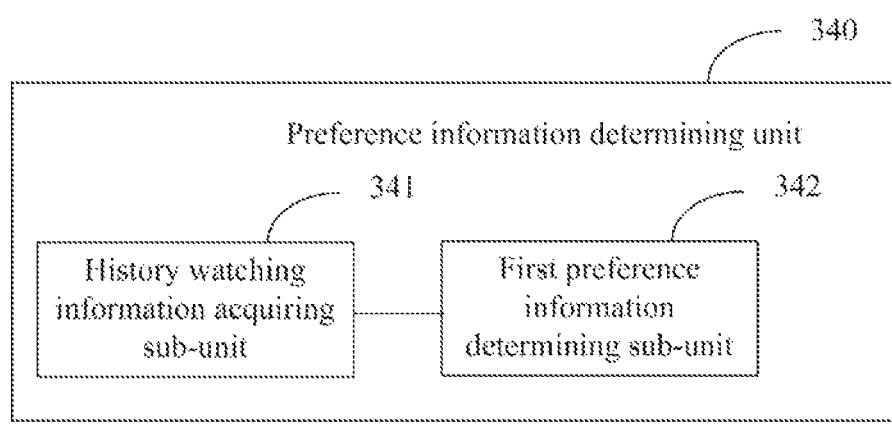

As shown in FIG. 13, FIG. 13 is a block diagram of still another apparatus for controlling a display device according to an exemplary aspect of the present disclosure. The aspect is based on the aspect as shown in FIG. 3, the preference information determining unit 340 includes a history watching information acquiring sub-unit 341 and a first preference information determining sub-unit 342.

The history watching information acquiring sub-unit 341 is configured to read history watching information of the user in a third history period according to the identity information of the user; and the first preference information determining sub-unit 342 is configured to analyze the history watching information to acquire the preference information of the user.

It may be seen from the aspect above that, in the present disclosure, history watching information of the user in a third history period is read according to the identity information of the user; and the history watching information is analyzed to acquire the preference information of the user, thereby improving the accuracy in acquiring the preference information.

Figure 14:
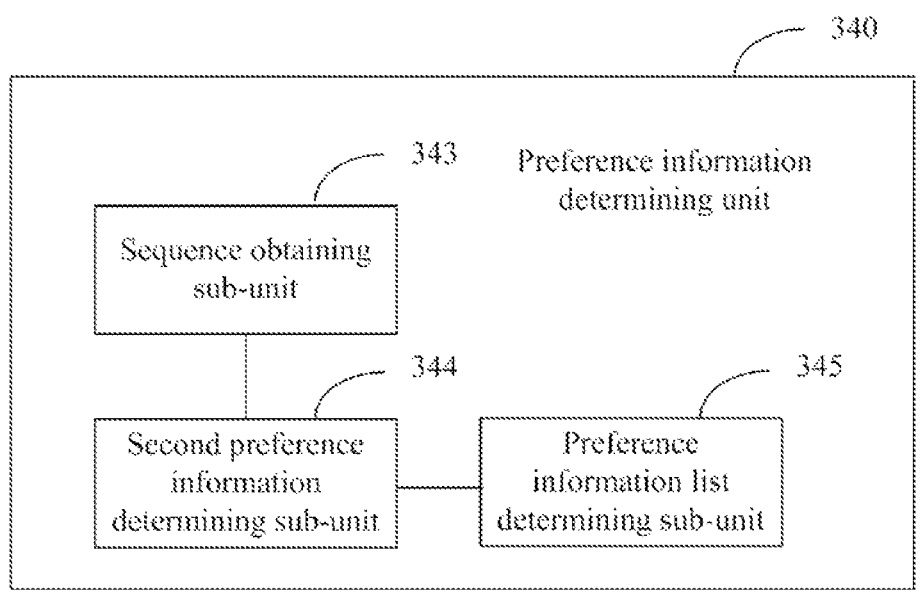

As shown in FIG. 14, FIG. 14 is a block diagram of still another apparatus for controlling a display device according to an exemplary aspect of the present disclosure. The aspect is based on the aspect as shown in FIG. 3, the preference information determining unit 340 includes a sequence obtaining sub-unit 343, a second preference information determining sub-unit 344 and a preference information list determining sub-unit 345.

The sequence obtaining sub-unit 343 is configured to acquire, when there are at least two users on the intelligent mat, a sequence that the at least two users contact the intelligent mat;

the second preference information determining sub-unit 344 is configured to determine preference information corresponding to each of the at least two users according to the identity information of the at least two users; and the preference information list determining sub-unit 345 is configured to sort the preference information of the at least two users according to the sequence to acquire a preference information list.

It may be seen from the aspect above that, in the aspect of the present disclosure, a sequence of preference information is determined according to a sequence that users contact the intelligent mat, so that a user who contacts the pad first has the priority to view his/her preference information, thus improving user experience.

Figure 15:
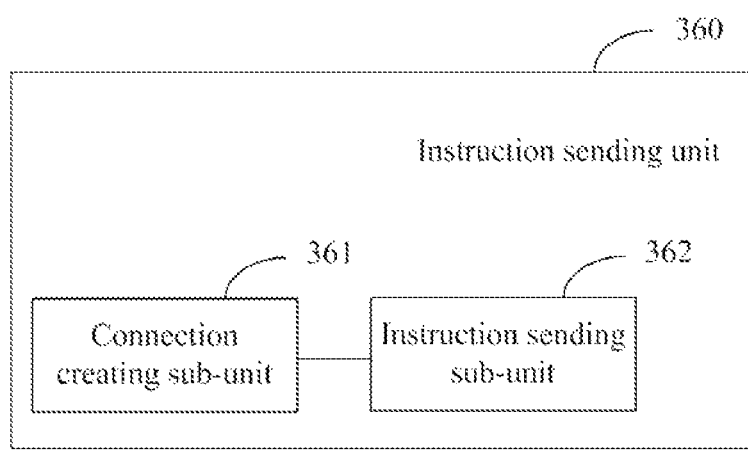

As shown in FIG. 15, FIG. 15 is a block diagram of still another apparatus for controlling a display device according to an exemplary aspect of the present disclosure. The aspect is based on the aspect as shown in FIG. 3, the instruction sending unit 360 includes a connection creating sub-unit 361 and an instruction sending sub-unit 362.

The connection creating sub-unit 361 is configured to create a wireless connection with the display device associated with the intelligent mat; and the instruction sending sub-unit 362 is configured to send a booting instruction and the instruction for displaying the preference information to the display device through the wireless connection.

It may be seen from the aspect above that, in the aspect of the present disclosure, a booting instruction and the instruction for displaying the preference information are sent to the display device so as to implement automatic booting, display preference information and improve user experience.

Accordingly, the present disclosure further provides an apparatus, the apparatus includes a processor, and a memory configured to store an instruction executable by the processor, wherein the processor is configured to:

determine identity information of a user on an intelligent mat;

determine preference information of the user according to the identity information of the user; and send an instruction for displaying the preference information to a display device associated with the intelligent pad.

For details of processes for implementing functions and effect of each unit in the apparatus above, please specifically refer to processes for implementing corresponding steps in the method above, and repeated description will not be provided here, wherein the apparatus may be a terminal. For example, the apparatus may be specifically a smart phone, a tablet computer, a Personal Digital Assistant (PDA) and so on, or may be also an intelligent mat, that is, a chip or a device for processing information is arranged in the intelligent pad. The intelligent pad may determine identity information of a user on the intelligent mat, determines preference information of the user according to the identity information of the user, and sends an instruction for displaying the preference information to a display device, thus controlling the display device.

Related parts of the apparatus aspects substantially corresponding to the method aspects may refer to the some description of the method aspects. The apparatus aspects described above are only schematic, wherein the units described as separate components may be or may not be physically separate. Components shown as units may be or may not be physical units, that is, may be located in one place, or may also be distributed on multiple network units. Some or all of the modules may be selected to achieve the objectives of the solutions of the aspects of the present disclosure according to an actual requirement. A person of ordinary skills in the art can understand implement the aspects of the present disclosure without any innovative effort.

Accordingly, the aspects of the present disclosure further provides an intelligent mat, the intelligent pad includes:

sensors and a transmitting apparatus, wherein the sensors are uniformly arranged in a network pattern on the intelligent mat;

the sensors are configured to acquire data on the intelligent mat;

the transmitting apparatus is configured to transmit the data acquired by the sensors to a terminal so as to enable the terminal to determine that an object on the intelligent pad is a user according to the data, and control a display device associated with the intelligent pad to display preference information of the user.

The sensors may be pressure sensors or temperature sensors. When the sensors are pressure sensors, the pressure sensors detect pressure information on the intelligent pad and each pressure sensor corresponds to a detection point. When the sensors are temperature sensors, the temperature sensors detect the temperature of the object on the intelligent pad.

The data acquired by the intelligent pad is transmitted to the terminal (such as a mobile phone, a tablet computer and so on) and the terminal may nm the method for controlling the display device of the aspects of the present disclosure.

Figure 16:
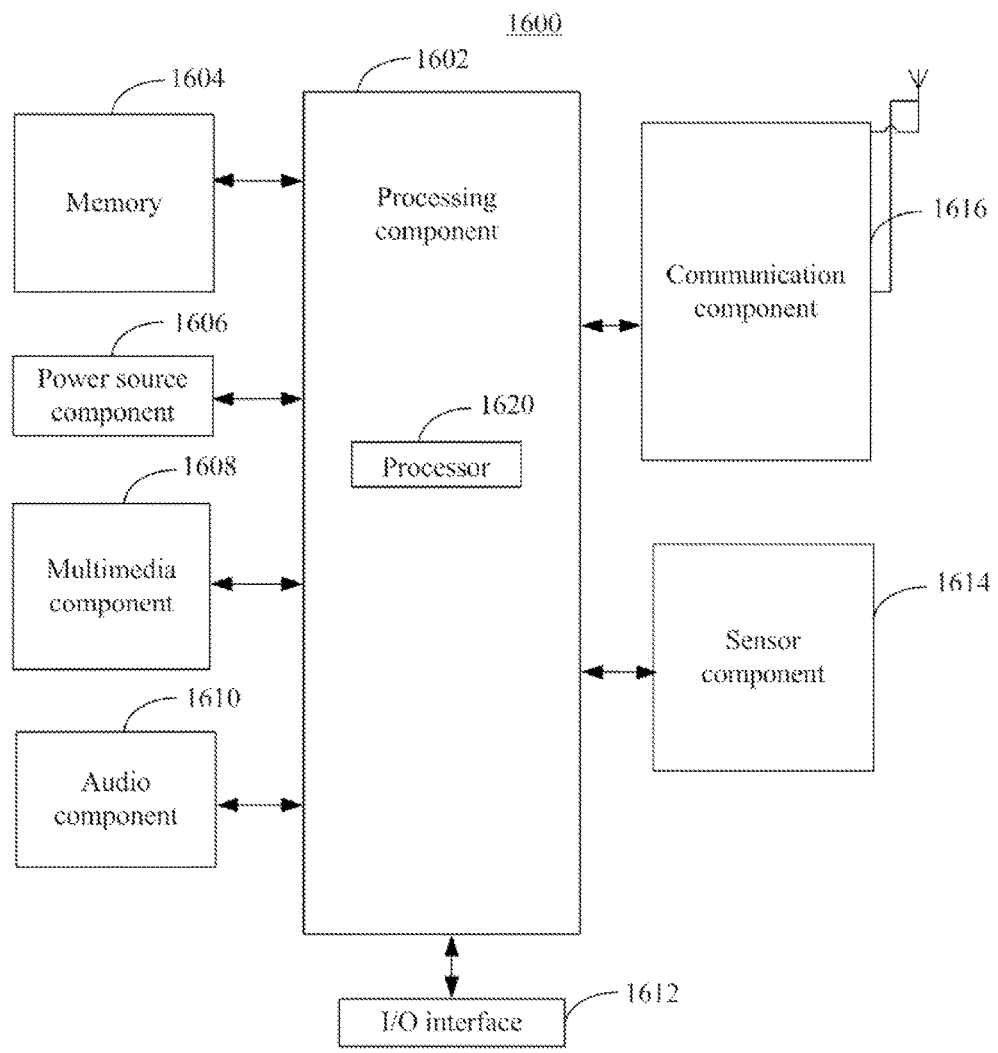
FIG. 16 is a structural diagram of a control apparatus applied to a display device according to an exemplary aspect of the present disclosure.

As shown in FIG. 16, FIG. 16 is a structural diagram of a control apparatus 1600 applied to a display device according to an exemplary aspect of the present disclosure. For example, the apparatus 1600 may be a mobile phone, a computer, a digital broadcasting terminal, a message transceiver, a games console, a tablet device, a medical device, fitness equipment, a personal digital assistant and so on having a routing function.

Referring to FIG. 16, the apparatus 1600 may include one or more of the following components: a processing component 1602, a memory 1604, a power source component 1606, a multimedia component 1608, an audio component 1610, an Input/Output (I/O) interface 1612, a sensor component 1614 and a communication component 1616.

Generally, the processing component 1602 controls overall operations of the apparatus 1600, such as operations associated with display, a telephone call, data communication, a camera operation and a recording operation. The processing component 1602 may include one or more processors 1620 to execute instructions so as to perform all or part of the steps of the method. Besides, the processing component 1602 may include one or more modules which facilitate interaction between the processing component 1602 and other components. For example, the processing component 1602 may include a multimedia module to facilitate interaction between the multimedia component 1608 and the processing component 1602.

The memory 1604 is configured to store various types of data so as to support operations in the apparatus 1600.

Examples of these data include an instruction of any App or method operated on the apparatus 1600, data of contacts, data of a telephone directory, a message, a picture, a video and so on. The memory 1604 may be implemented by a volatile or non-volatile storage apparatus of any type or a combination thereof, such as a Static Random-Access Memory (SRAM), an Electrically Erasable Programmable Read-Only Memory (EEPROM), an Erasable Programmable Read-Only Memory (EPROM), a Programmable Read-Only Memory (PROM), a Read-Only Memory (ROM), a magnetic memory, a flash memory, a magnetic disk or an optical disk.

The power source component 1606 provides power for various components of the apparatus 1600. The power source component 1606 may include a power source management system, one or more power sources, and other components associated with power generation, management and distribution of the apparatus 1600.

The multimedia component 1608 includes a screen providing an output interface between the apparatus 1600 and a user. In some aspects, the screen may include a Liquid Crystal Display (LCD) and a Touch Panel (TP). If the screen includes a TP, the screen may be implemented as a touch screen to receive an input signal from the user. The TP includes one or more touch sensors so as to sense a touch, a slide, and a gesture on the TP. The touch sensor may not only sense a touch or a boundary of a slide, but also detect a duration and a pressure related to the touch or the slide. In some aspects, the multimedia component 1608 includes a front camera and/or a rear camera. When the apparatus 1600 is in an operation mode, such as a camera mode or a video mode, the front camera and/or the rear camera may receive external multimedia data. Each front camera and each rear camera may be a fixed optical lens system or may be provided with a focal distance or an optical zooming capability.

The audio component 1610 is configured to output and/or input an audio signal. For example, the audio component 1610 includes a Microphone (MIC). When the apparatus 1600 is in an operation mode, such as a calling mode, a recording mode and a voice recognition mode, the MIC is configured to receive an external audio signal. The received audio signal may be further stored in the memory 1604 or sent by the communication component 1616. In some aspects, the audio component 1610 further includes a loudspeaker, configured to output the audio signal.

The I/O interface 1612 provides an interface between the processing component 1602 and a peripheral interface module. The peripheral interface module may be a keyboard, a click wheel, a button and so on. These buttons may include, but are not limited to a homepage button, a volume button, a start button and a lock button.

The sensor component 1614 includes one or more sensors configured to provide evaluation of states of various aspects for the apparatus 1600. For example, the sensor component 1614 may detect an on/off state of the apparatus 1600, and the relative locations of the components. For example, the components are a display and a keypad of the apparatus 1600. The sensor component 1614 may further detect a change of the location of the apparatus 1600 or a change of the location of a component of the apparatus 1600, the existence or absence of contact between the user and the apparatus 1600, the orientation or acceleration/deceleration of the apparatus 1600 and a change in the temperature of the apparatus 1600. The sensor component 1614 may include a proximity sensor, configured to detect the existence of a nearby object when there is no any physical contact. The sensor component 1614 may further include an optical sensor, such as a Complementary Metal Oxide Semiconductor (CMOS) or Charge Coupled Device (CCD) image sensor used in an imaging App. In some aspects, the sensor component 1614 may further include an acceleration sensor, a gyro sensor, a magnetic sensor, a pressure sensor or a temperature sensor.

The communication component 1616 is configured to facilitate wired or wireless communication between the apparatus 1600 and other apparatuses. The apparatus 1600 may access a wireless network based on a communication standard, such as Wireless Fidelity (WiFi), the second Generation (2G) or the third Generation (3G), or a combination thereof. In an exemplary aspect, the communication component 1616 receives a broadcast signal from an external broadcast management system or broadcast related information through a broadcast channel. In an exemplary aspect, the communication component 1616 further includes a Near Field Communication (NFC) module so as to promote short distance communication. For example, the NFC module may be implemented based on a Radio-frequency Identification (RFID) technology, an Infrared Data Association (IrDA) technology, an Ultra Wide Band (UWB) technology, a Bluetooth (BT) technology and other technologies.

In an exemplary aspect, the apparatus 1600 may be implemented by one or more Application Specific Integrated Circuits (ASIC), Digital Signal Processors (DSP), Digital Signal Processing Apparatus (DSPD), Programmable Logic Apparatus (PLD), Field Programmable Gate Arrays (FPGA), controllers, microcontrollers, microprocessors, or other electronic components, so as to execute the method above.

A non-temporary computer readable storage medium including an instruction is further provided in an exemplary aspect, such as the memory 1604 including an instruction. The instruction may be executed by the processor 1620 of the apparatus 1600 so as to implement the methods above. For example, the non-temporary computer readable storage medium may be a ROM, a Random-Access Memory (RAM), a Compact Disc-ROM (CD-ROM), a magnetic tape, a floppy disk, an optical data memory and so on.

A non-temporary computer readable storage medium enables a terminal to execute a method for controlling a displaying apparatus when an instruction in the storage medium is executed by a processor of the terminal. The method includes that identity information of a user on an intelligent pad is determined, preference information of the user is determined according to the identity information of the user; and an instruction for displaying the preference information is sent to a display device associated with the intelligent pad.

Other aspects of the present disclosure will be apparent to those skilled in the art from consideration of the specification and practice of the aspects of the present disclosure disclosed here. The application aims to cover any variations, uses or adaptive changes of the aspects of the present disclosure. These variations, uses or adaptive changes follow general principles of the aspects of the present disclosure and include such departures from the aspects of the present disclosure as common general knowledge or conventional technical means in the art. The specification and aspects are only considered exemplary, and the true scope and spirit of the aspects of the present disclosure will be indicated by the following claims.

It is to be understood that the aspects of the present disclosure is not limited to the precise structures that have been described above or illustrated in the accompanying drawings, and various modifications and changes may be made without departing from the scope of the present disclosure. The scope of the aspects of the present disclosure is limited by the appended claims.

INDUSTRY APPLICABILITY

The aspects of the present disclosure determine identity information of a user on an intelligent mat, determines preference information of the user according to the identity information of the user, and then sends an instruction for displaying the preference information to a display device associated with the intelligent mat, so that the preference information of the user on the intelligent pad is displayed and the user does not need to select the preference information manually from a large amount of data, thus improving searching efficiency and bringing more convenience to the user.

The aspects of the present disclosure first determines whether an object on the intelligent pad is a user, and when the object is a user, determines identity information of the user, so that other objects which are not human bodies are filtered, only a user is identified to determine identity information thereof while other objects are not identified, thus improving the efficiency in determining identity information.

In the aspects of the present disclosure, temperature data of the object on the intelligent pad is acquired and compared with a pre-stored range of human body temperature, and the object is determined to be a user only when the temperature data is in the pre-stored range of human body temperature, thereby improving the judgment efficiency.

In the aspects of the present disclosure, pressure information on the intelligent pad is acquired, and the shape of an object on the intelligent pad is determined according to points where the pressure information is capable of being acquired on the intelligent mat, so that the determined shape can be compared with a pre-stored shape of a human body to judge whether the object on the intelligent pad is a user, thus improving the judgment efficiency.

In the aspects of the present disclosure, pressure information on the intelligent pad is acquired, a stressed area is determined according to points where the pressure information is capable of being acquired on the intelligent mat, the ratio of the pressure information to the stressed area is calculated to obtain the density of the object on the intelligent mat, and the object is determined to be a user when the calculated density is in a pre-stored range of human body density. Whether the object on the intelligent pad is a user is determined according to the density, thus improving the judgment accuracy.

In the aspects of the present disclosure, difference values between physiological parameters and sample physiological parameters in a data list are calculated, a target difference value in an allowable fluctuation range is selected from the difference values, so as to determine the identity information of the user, thus determining the identity information according to the physiological parameters. Since the physiological parameters have been determined when the user is determined, it is unnecessary to acquire other data when the identity information is determined, thus saving resources.

In the aspects of the present disclosure, history physiological parameters are averaged to obtain sample physiological parameters, and corresponding relations between identity information of users and sample physiological parameters are created and a data list is obtained, thereby improving the reliability of the sample physiological parameters.

In the aspects of the present disclosure, an exercise parameter of the user within a second history period is acquired, the exercise parameter is compared with an upper exercise limit and a lower exercise limit of the user; and an allowable fluctuation range of the exercise parameter of the user is determined according to a comparison result. The allowable fluctuation range is adjusted according to the exercise parameter, which considers a factor that the physiological parameters change with the exercise parameter, thereby improving the accuracy of the allowable fluctuation range and further improving the accuracy in determining the identity information.

In the aspects of the present disclosure, the identity information of the user is determined by comparing acquired biologic characteristic information with pre-stored biologic characteristic information of a valid user, thereby improving the determining accuracy.

In the aspects of the present disclosure, account information used by the user to log in an App on a terminal is read; and the identity information of the user is determined according to the account information, thereby improving the determining efficiency and accuracy.

In the aspects of the present disclosure, history watching information of the user in a third history period is read according to the identity information of the user; and the history watching information is analyzed to acquire the preference information of the user, thereby improving the accuracy in acquiring the preference information.

In the aspects of the present disclosure, a sequence of preference information is determined according to a sequence that users contact the intelligent mat, so that a user who contacts the pad first has the priority to view his/her preference information, thus improving user experience.

In the aspects of the present disclosure, a booting instruction and the instruction for displaying the preference information are sent to the display device so as to implement automatic booting, display preference information and improve user experience.

It is noted that the various modules, sub-modules, units, and components in the present disclosure can be implemented using any suitable technology. For example, a module may be implemented using circuitry, such as an integrated circuit (IC). As another example, a module may be implemented as a processing circuit executing software instructions.

Other aspects of the present disclosure will be apparent to those skilled in the art from consideration of the specification and practice of the present disclosure. This application is intended to cover any variations, uses, or adaptations of the present disclosure following the general principles thereof and including such departures from the present disclosure as come within known or customary practice in the art. It is intended that the specification and examples be considered as exemplary only, with a true scope and spirit of the present disclosure being indicated by the following claims.

It will be appreciated that the present disclosure is not limited to the precise structures that have been described above and illustrated in the accompanying drawings, and that various modifications and changes may be made without departing from the scope thereof. It is intended that the scope of the present disclosure only be limited by the appended claims.

What is claimed is:

1. A method for controlling a display device via a terminal, comprising:
   detecting an object on a pad;
   determining whether the object is a user;
   determining an identity of the user when it is determined that the object is the user, wherein determining the identity of the user includes:
      calculating difference values between a first set of measured physiological parameters and a second set of preset physiological parameters including an upper exercise limit and a lower exercise limit that are stored in a data list, wherein the first set of measured physiological parameters and the second set of preset physiological parameters include at least one of pressure data, stressed area, and density;
      selecting a target difference value for an allowable fluctuation range from the difference values, wherein the allowable fluctuation range is determined by (i) acquiring an exercise parameter of the user within a first time period, wherein the exercise parameter corresponds to a total amount of exercise within the first time period and the total amount of the exercise causes a change in the first set of measured physiological parameters, (ii) comparing the exercise parameter with the upper exercise limit and the lower exercise limit of the user, and (iii) determining the allowable fluctuation range based on a result of the comparison;
      determining a target physiological parameter based on the target difference value; and
      acquiring the identity of the user based on the target physiological parameter, wherein the data list includes relationships between physiological parameters and identities of users;
   determining at least one user preference associated with the user based on the identity of the user; and
   transmitting, to the display device, at least one instruction to display information associated with the at least one user preference.

2. The method according to claim 1, wherein determining whether the object is the user includes:
   acquiring temperature data of the object;
   determining whether the temperature data is within a pre-stored temperature range of a human body; and
   determining that the object is a person when the temperature data is determined to be within the pre-stored temperature range of the human body.

3. The method according to claim 1, wherein determining whether the object is the user includes:
   acquiring pressure data from a plurality of locations on the pad;
   determining a shape of the object based on the pressure data;
   comparing the determined shape with a pre-stored shape of a human body to obtain a first similarity; and
   determining that the object is a person when the first similarity is greater than a first threshold.

4. The method according to claim 1, wherein determining whether the object is the user includes:
   acquiring pressure data from a plurality of points on the pad;
   determining a stressed area based on the pressure data;
   determining a density of the object based on a ratio of the pressure data to the stressed area;
   determining whether the density of the object is within a pre-stored range of densities of a human body; and
   determining that the object is a person when the density is within the pre-stored range of densities of the human body.

5. The method according to claim 1, further comprising:
   acquiring historical physiological parameters for each of a plurality of users in a second time period from a database;
   calculating an average of the historical physiological parameters of each of the plurality of users to obtain individualized sets of physiological parameters for the plurality of users;
   establishing relationships between the identities of the users and the individualized sets of physiological parameters by associating each of the identities of the users with a respective one of the individualized sets of physiological parameters; and
   generating the second set of preset physiological parameters based on the relationships.

6. The method according to claim 1, wherein determining the at least one user preference includes:
   accessing historical watching information of the user in a second time period according to the identity of the user; and
   analyzing the historical watching information to acquire the at least one user preference of the user.

7. The method according to claim 1, wherein determining the at least one user preference includes:
   determining that a plurality of users are in contact with the pad;
   determining a sequence of contact by the plurality of users with the pad;
   determining a plurality of user preferences corresponding to the plurality of users based on respective identities of each of the plurality of users; and
   sorting the plurality of user preferences based on the sequence of the contact to acquire a preference information list.

8. The method according to claim 1, wherein transmitting the at least one instruction includes:
   establishing a wireless connection with the display device; and
   transmitting the at least one instruction including a booting instruction to the display device via the wireless connection.

9. An apparatus, comprising:
   a processor; and
   a memory configured to store an instruction executable by the processor, wherein the processor is configured to:
      detect an object on a pad;
      determine whether the object is a user;
      determine an identity of the user when it is determined that the object is the user, wherein to determine the identity of the user, the processor is configured to:
         calculate difference values between a first set of measured physiological parameters and a second set of preset physiological parameters including an upper exercise limit and a lower exercise limit that are stored in a data list, wherein the first set of measured physiological parameters and the second set of preset physiological parameters include at least one of pressure data, stressed area, and density;
         select a target difference value for an allowable fluctuation range from the difference values, wherein the allowable fluctuation range is determined by (i) acquiring an exercise parameter of the user within a first time period, wherein the exercise parameter corresponds to a total amount of exercise within the first time period and the total amount of the exercise causes a change in the first set of measured physiological parameters, (ii) comparing the exercise parameter with the upper exercise limit and the lower exercise limit of the user, and (iii) determining the allowable fluctuation range based on a result of the comparison;

determine a target physiological parameter based on the target difference value; and acquire the identity of the user based on the target physiological parameter, wherein the data list includes relationships between physiological parameters and identities of users;

determine at least one user preference associated with the user based on the identity of the user; and transmit, to the display device, at least one instruction to display information associated with the at least one user preference.

10. The apparatus according to claim 9, wherein the processor is further configured to:

acquire historical physiological parameters for each of a plurality of users in a second time period from a database;

calculate an average of the historical physiological parameters of each of the plurality of users to obtain individualized sets of physiological parameters for the plurality of users;

establish relationships between the identities of the users and the individualized sets of physiological parameters by associating each of the identities of the users with a respective one of the individualized sets of physiological parameters; and generate the second set of preset physiological parameters based on the relationships.

11. An apparatus comprising:

a pad;

a plurality of sensors uniformly arranged in a network pattern on the pad, wherein the sensors are configured to acquire data from the pad; and a transmitter configured to transmit the data to a terminal, wherein the sensors are configured to detect an object on the pad, wherein the terminal is configured to:

determine whether the object is a user;

determine an identity of the user when it is determined that the object is the user, wherein to determine the identity of the user, the terminal is configured to:

calculate difference values between a first set of measured physiological parameters and a second set of preset physiological parameters including an upper exercise limit and a lower exercise limit that are stored in a data list, wherein the first set of measured physiological parameters and the second set of preset physiological parameters include at least one of pressure data, stressed area, and density;

select a target difference value for an allowable fluctuation range from the difference values, wherein the allowable fluctuation range is determined by (i) acquiring an exercise parameter of the user within a first time period, wherein the exercise parameter corresponds to a total amount of exercise within the first time period and the total amount of the exercise causes a change in the first set of measured physiological parameters, (ii) comparing the exercise parameter with the upper exercise limit and the lower exercise limit of the user, and (iii) determining the allowable fluctuation range based on a result of the comparison;

determine a target physiological parameter based on the target difference value; and acquire the identity of the user based on the target physiological parameter, wherein the data list includes relationships between physiological parameters and identities of users;

determine at least one user preference associated with the user based on the identity of the user; and transmit, to the display device, at least one instruction to display information associated with the at least one user preference.

* * * * *